(12) United States Patent
Burkholz et al.

(10) Patent No.: US 11,793,986 B2
(45) Date of Patent: Oct. 24, 2023

(54) SEPTUM HOUSING

(71) Applicant: Becton, Dickinson and Company, Franklin Lakes, NJ (US)

(72) Inventors: Jonathan Karl Burkholz, Salt Lake City, UT (US); Daniel Kirk Hyer, Alpine, UT (US); Bin Wang, Sandy, UT (US); Tyler Warner, Bluffdale, UT (US); Ralph L. Sonderegger, Farmington, UT (US); Eric Davis, Saratoga Springs, UT (US); Carl Ellis, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 439 days.

(21) Appl. No.: 16/269,291

(22) Filed: Feb. 6, 2019

(65) Prior Publication Data

US 2019/0167966 A1    Jun. 6, 2019

Related U.S. Application Data

(62) Division of application No. 15/286,278, filed on Oct. 5, 2016, now Pat. No. 10,238,852.

(51) Int. Cl.
*A61M 39/04* (2006.01)
*A61M 25/06* (2006.01)
(Continued)

(52) U.S. Cl.
CPC ........ *A61M 39/04* (2013.01); *A61M 25/0606* (2013.01); *A61M 39/00* (2013.01);
(Continued)

(58) Field of Classification Search
None
See application file for complete search history.

(56) References Cited

U.S. PATENT DOCUMENTS 3,046,984 A    7/1962   Eby
3,547,119 A    12/1970  Hall et al.
(Continued)

FOREIGN PATENT DOCUMENTS

CA    2133053       3/1995
CA    3002701 C     5/2017
(Continued)

OTHER PUBLICATIONS

Translation of Haindl et al. (DE 3834600) (Year: 1989).*
(Continued)

*Primary Examiner* — Nilay J Shah
(74) *Attorney, Agent, or Firm* — KIRTON MCCONKIE; Whitney Blair; Kevin Stinger

(57) ABSTRACT

A catheter assembly may include a catheter adapter, a septum housing, and a septum. The catheter adapter may include a distal end, a proximal end, an inner wall extending between the distal end and the proximal end, and a lumen formed by the inner wall. The septum housing may include one or more protrusions and may be secured to the inner wall by one or more of the following: an interference fit between the one or more protrusions and the inner wall, a snap fit between the one or more protrusions and the inner wall, and bonding between the one or more protrusions and the inner wall. The septum may be at least partially disposed within the septum housing and configured to at least substantially seal the lumen.

8 Claims, 11 Drawing Sheets

(51) Int. Cl.
  *A61M 39/00* (2006.01)
  *A61M 39/06* (2006.01)
  *A61M 39/10* (2006.01)
(52) U.S. Cl.
  CPC ......... *A61M 39/06* (2013.01); *A61M 39/0606* (2013.01); *A61M 2039/0036* (2013.01); *A61M 2039/0072* (2013.01); *A61M 2039/062* (2013.01); *A61M 2039/066* (2013.01); *A61M 2039/0626* (2013.01); *A61M 2039/1072* (2013.01)

(56) References Cited

U.S. PATENT DOCUMENTS

| | | |
|---|---|---|
| 3,589,361 A | 6/1971 | Loper et al. |
| 3,827,434 A | 8/1974 | Thompson et al. |
| 3,853,127 A | 12/1974 | Spademan |
| 3,859,998 A | 1/1975 | Thomas et al. |
| 4,003,403 A | 1/1977 | Nehring |
| 4,043,346 A | 8/1977 | Mobley et al. |
| 4,099,528 A | 7/1978 | Sorenson et al. |
| 4,106,491 A * | 8/1978 | Guerra ............... A61B 5/15003 251/149.2 |
| 4,149,539 A | 4/1979 | Cianci |
| 4,172,448 A | 10/1979 | Brush |
| 4,177,809 A | 12/1979 | Moorehead |
| 4,193,399 A | 3/1980 | Robinson |
| 4,200,096 A | 4/1980 | Charvin |
| 4,269,186 A | 5/1981 | Loveless et al. |
| 4,311,137 A | 1/1982 | Gerard |
| 4,317,445 A | 3/1982 | Robinson |
| 4,326,519 A | 4/1982 | D'Alo et al. |
| 4,353,369 A | 10/1982 | Muetterties et al. |
| 4,362,156 A | 12/1982 | Feller, Jr. et al. |
| 4,365,630 A | 12/1982 | McFarlane |
| 4,387,879 A | 6/1983 | Tauschinski |
| 4,419,094 A | 12/1983 | Patel |
| 4,445,893 A | 5/1984 | Bodicky |
| 4,449,693 A | 5/1984 | Gereg |
| 4,496,348 A | 1/1985 | Genese et al. |
| 4,525,157 A | 6/1985 | Vaillancourt |
| 4,531,935 A | 7/1985 | Berryessa |
| 4,682,980 A | 7/1987 | Suzuki |
| 4,701,162 A | 10/1987 | Rosenberg |
| 4,703,761 A | 11/1987 | Rathbone et al. |
| 4,710,173 A | 12/1987 | McFarlane |
| 4,758,225 A | 7/1988 | Cox et al. |
| 4,765,588 A | 8/1988 | Atkinson |
| 4,772,264 A | 9/1988 | Cragg |
| 4,813,939 A | 3/1989 | Marcus |
| 4,834,708 A | 5/1989 | Pillari |
| 4,842,591 A | 6/1989 | Luther |
| 4,874,377 A | 10/1989 | Newgard et al. |
| 4,894,052 A | 1/1990 | Crawford |
| 4,917,668 A | 4/1990 | Haindl |
| 4,917,671 A | 4/1990 | Chang |
| 4,925,444 A | 5/1990 | Orkin et al. |
| 4,935,010 A | 6/1990 | Cox et al. |
| 4,950,257 A | 8/1990 | Hibbs et al. |
| 4,966,586 A | 10/1990 | Vaillancourt |
| D315,822 S | 3/1991 | Ryan |
| 5,007,898 A * | 4/1991 | Rosenbluth ........... A61M 29/02 604/101.05 |
| 5,032,116 A | 7/1991 | Peterson et al. |
| 5,041,097 A | 8/1991 | Johnson |
| 5,053,014 A | 10/1991 | Van Heugten |
| 5,057,087 A | 10/1991 | Harmon |
| 5,059,186 A | 10/1991 | Yamamoto et al. |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,135,504 A | 8/1992 | McLees |
| 5,154,703 A | 10/1992 | Bonaldo |
| 5,156,596 A | 10/1992 | Balbierz et al. |
| 5,176,653 A | 1/1993 | Metais |
| 5,176,662 A | 1/1993 | Bartholomew et al. |
| 5,186,712 A | 2/1993 | Kelso |
| 5,201,717 A | 4/1993 | Wyatt et al. |
| 5,211,634 A | 5/1993 | Vaillancourt |
| 5,215,525 A | 6/1993 | Sturman |
| 5,215,528 A | 6/1993 | Purdy et al. |
| 5,215,529 A | 6/1993 | Fields et al. |
| 5,226,883 A | 7/1993 | Katsaros et al. |
| 5,234,410 A | 8/1993 | Graham et al. |
| 5,242,411 A | 9/1993 | Yamamoto et al. |
| 5,254,097 A | 10/1993 | Schock et al. |
| 5,267,971 A | 12/1993 | Brimhall |
| 5,269,764 A | 12/1993 | Vetter et al. |
| 5,273,546 A | 12/1993 | McLaughlin et al. |
| 5,290,222 A | 3/1994 | Feng et al. |
| 5,290,246 A | 3/1994 | Yamamoto et al. |
| 5,295,969 A | 3/1994 | Fischell et al. |
| 5,300,045 A | 4/1994 | Plassche, Jr. et al. |
| 5,306,243 A | 4/1994 | Bonaldo |
| 5,312,359 A | 5/1994 | Wallace |
| 5,328,482 A | 7/1994 | Sircom et al. |
| 5,330,435 A | 7/1994 | Vaillancourt |
| 5,342,315 A | 8/1994 | Rowe et al. |
| 5,350,363 A | 9/1994 | Goode et al. |
| 5,352,205 A | 10/1994 | Dales et al. |
| 5,354,281 A | 10/1994 | Chen |
| 5,356,381 A | 10/1994 | Ensminger et al. |
| 5,368,029 A | 11/1994 | Holcombe et al. |
| 5,405,323 A | 4/1995 | Rogers et al. |
| 5,447,501 A | 9/1995 | Karlsson et al. |
| 5,456,675 A | 10/1995 | Wolbring et al. |
| 5,458,658 A | 10/1995 | Sircom |
| 5,487,728 A | 1/1996 | Vaillancourt |
| 5,498,241 A | 3/1996 | Fabozzi |
| 5,509,912 A | 4/1996 | Vaillancourt et al. |
| 5,520,666 A | 5/1996 | Choudhury et al. |
| 5,542,932 A | 8/1996 | Daugherty |
| 5,549,566 A | 8/1996 | Elias et al. |
| 5,549,576 A | 8/1996 | Patterson et al. |
| 5,549,577 A | 8/1996 | Siegel et al. |
| 5,562,631 A | 10/1996 | Bogert |
| 5,562,633 A | 10/1996 | Wozencroft |
| 5,573,510 A | 11/1996 | Isaacson |
| 5,575,769 A | 11/1996 | Vaillancourt |
| 5,575,777 A | 11/1996 | Cover et al. |
| 5,584,809 A | 12/1996 | Gaba |
| 5,599,310 A | 2/1997 | Bogert |
| 5,601,536 A | 2/1997 | Crawford et al. |
| 5,613,663 A | 3/1997 | Schmidt et al. |
| 5,651,772 A | 7/1997 | Arnett |
| 5,657,963 A | 8/1997 | Hinchliffe et al. |
| 5,676,656 A | 10/1997 | Brimhall |
| 5,690,612 A | 11/1997 | Lopez et al. |
| 5,690,619 A | 11/1997 | Erskine |
| 5,697,907 A | 12/1997 | Gaba |
| 5,697,914 A | 12/1997 | Brimhall |
| 5,697,915 A | 12/1997 | Lynn |
| 5,699,821 A | 12/1997 | Paradis |
| 5,700,244 A | 12/1997 | Kriesel |
| 5,700,250 A | 12/1997 | Erskine |
| 5,704,919 A | 1/1998 | Kraus et al. |
| 5,718,688 A | 2/1998 | Wozencroft |
| 5,730,123 A | 3/1998 | Lorenzen et al. |
| 5,738,144 A | 4/1998 | Rogers |
| 5,749,856 A | 5/1998 | Zadini et al. |
| 5,749,861 A | 5/1998 | Guala et al. |
| 5,772,636 A | 6/1998 | Brimhall et al. |
| 5,800,399 A | 9/1998 | Bogert et al. |
| 5,806,831 A | 9/1998 | Paradis |
| 5,810,780 A | 9/1998 | Brimhall et al. |
| 5,810,835 A | 9/1998 | Ryan et al. |
| 5,817,069 A | 10/1998 | Arnett |
| 5,843,046 A | 12/1998 | Motisi et al. |
| 5,853,393 A | 12/1998 | Bogert |
| 5,882,345 A | 3/1999 | Yoon |

(56) References Cited

U.S. PATENT DOCUMENTS

| | | | |
|---|---|---|---|
| 5,911,710 A | 6/1999 | Barry et al. | |
| 5,935,109 A | 8/1999 | Donnan | |
| 5,935,110 A | 8/1999 | Brimhall | |
| 5,947,932 A | 9/1999 | Desecki et al. | |
| 5,954,698 A | 9/1999 | Pike | |
| 5,961,497 A | 10/1999 | Larkin | |
| 5,967,490 A | 10/1999 | Pike | |
| 6,039,302 A | 3/2000 | Cote, Sr. et al. | |
| 6,056,726 A | 5/2000 | Isaacson | |
| 6,077,244 A | 6/2000 | Botich et al. | |
| 6,117,108 A | 9/2000 | Woehr et al. | |
| 6,142,981 A | 11/2000 | Heck et al. | |
| 6,156,010 A | 12/2000 | Kuracina et al. | |
| 6,171,287 B1 | 1/2001 | Lynn et al. | |
| 6,206,851 B1 | 3/2001 | Prosl | |
| 6,221,047 B1 | 4/2001 | Greene et al. | |
| 6,224,569 B1 | 5/2001 | Brimhall | |
| 6,273,869 B1 | 8/2001 | Vaillancourt | |
| 6,287,278 B1 | 9/2001 | Woehr et al. | |
| D451,599 S | 12/2001 | Crawford et al. | |
| D451,600 S | 12/2001 | Crawford et al. | |
| 6,379,332 B1 | 4/2002 | Van Landuyt | |
| D458,678 S | 6/2002 | Cindrich | |
| D458,994 S | 6/2002 | Cindrich | |
| 6,440,119 B1 | 8/2002 | Nakada et al. | |
| 6,461,362 B1 | 10/2002 | Halseth et al. | |
| 6,485,473 B1 | 11/2002 | Lynn | |
| 6,497,994 B1 | 12/2002 | Kafrawy | |
| 6,506,181 B2 | 1/2003 | Meng et al. | |
| D469,870 S | 2/2003 | Niermann et al. | |
| 6,565,542 B2 | 5/2003 | Kumar et al. | |
| 6,575,960 B2 | 6/2003 | Becker et al. | |
| 6,595,954 B1 | 7/2003 | Luther et al. | |
| 6,595,981 B2 | 7/2003 | Huet | |
| 6,616,630 B1 | 9/2003 | Woehr et al. | |
| 6,652,486 B2 | 11/2003 | Bialecki et al. | |
| 6,663,592 B2 | 12/2003 | Rhad et al. | |
| 6,689,102 B2 | 2/2004 | Greene | |
| 6,695,814 B2 | 2/2004 | Greene et al. | |
| 6,699,221 B2 | 3/2004 | Vaillancourt | |
| 6,709,419 B2 | 3/2004 | Woehr | |
| 6,719,726 B2 * | 4/2004 | Meng | A61M 39/045 604/164.07 |
| 6,740,063 B2 | 5/2004 | Lynn | |
| D491,266 S | 6/2004 | Cindrich et al. | |
| D492,031 S | 6/2004 | Cindrich et al. | |
| 6,749,588 B1 | 6/2004 | Howell et al. | |
| D492,774 S | 7/2004 | Cindrich et al. | |
| 6,837,884 B2 | 1/2005 | Woloszko | |
| 6,883,778 B1 | 4/2005 | Newton et al. | |
| 7,008,404 B2 | 3/2006 | Nakajima | |
| 7,347,839 B2 | 3/2008 | Hiejima | |
| 7,396,346 B2 | 7/2008 | Nakajima | |
| 7,470,254 B2 | 12/2008 | Basta et al. | |
| D592,302 S | 5/2009 | Stokes et al. | |
| 7,670,317 B2 | 3/2010 | Cindrich et al. | |
| 7,694,403 B2 | 4/2010 | Moulton | |
| 7,736,339 B2 | 6/2010 | Woehr et al. | |
| 7,905,856 B2 | 3/2011 | McGuckin, Jr. et al. | |
| 7,914,494 B2 | 3/2011 | Hiejima | |
| 8,066,670 B2 | 11/2011 | Cluff et al. | |
| 8,066,675 B2 | 11/2011 | Cindrich et al. | |
| 8,070,725 B2 | 12/2011 | Christensen | |
| 8,357,119 B2 | 1/2013 | Stout et al. | |
| 8,361,020 B2 | 1/2013 | Stout et al. | |
| 8,388,583 B2 | 3/2013 | Stout et al. | |
| 8,574,203 B2 | 11/2013 | Stout et al. | |
| 8,591,473 B2 | 11/2013 | Jones et al. | |
| 8,597,252 B2 | 12/2013 | Burkholz et al. | |
| 8,641,675 B2 | 2/2014 | Stout et al. | |
| 8,679,063 B2 | 3/2014 | Stout et al. | |
| 8,702,658 B2 | 4/2014 | Spearman | |
| D713,522 S | 9/2014 | Woehr et al. | |
| D819,802 S | 6/2018 | Burkholz et al. | |
| D835,262 S | 12/2018 | Burkholz et al. | |
| D837,368 S | 1/2019 | Burkholz et al. | |
| 10,245,416 B2 | 4/2019 | Harding et al. | |
| 10,639,455 B2 | 5/2020 | Burkholz et al. | |
| 10,744,305 B2 | 8/2020 | Burkholz et al. | |
| 10,814,106 B2 | 10/2020 | Garrison et al. | |
| 2001/0053895 A1 | 12/2001 | Vaillancourt | |
| 2002/0072712 A1 | 6/2002 | Nool et al. | |
| 2002/0082546 A1 | 6/2002 | Crank et al. | |
| 2002/0177814 A1 | 11/2002 | Chye et al. | |
| 2003/0083620 A1 | 5/2003 | Luther et al. | |
| 2003/0208165 A1 * | 11/2003 | Christensen | A61M 39/26 604/256 |
| 2004/0078003 A1 | 4/2004 | Smith et al. | |
| 2004/0092889 A1 | 5/2004 | Ferguson et al. | |
| 2004/0102735 A1 | 5/2004 | Moulton et al. | |
| 2004/0181192 A1 | 9/2004 | Cuppy | |
| 2004/0193112 A1 | 9/2004 | Glazier et al. | |
| 2004/0204681 A1 | 10/2004 | Thoresen et al. | |
| 2004/0225260 A1 | 11/2004 | Villa et al. | |
| 2004/0243060 A1 | 12/2004 | Rossi et al. | |
| 2004/0243061 A1 | 12/2004 | McGurk | |
| 2005/0015071 A1 | 1/2005 | Brimhall | |
| 2005/0251092 A1 | 11/2005 | Howell et al. | |
| 2005/0273019 A1 | 12/2005 | Conway et al. | |
| 2005/0277879 A1 | 12/2005 | Daga | |
| 2006/0163515 A1 | 7/2006 | Ruschke | |
| 2006/0264833 A1 | 11/2006 | Moulton | |
| 2007/0010796 A1 | 1/2007 | Moran et al. | |
| 2007/0043334 A1 | 2/2007 | Guala | |
| 2007/0083157 A1 | 4/2007 | Belley et al. | |
| 2007/0083162 A1 | 4/2007 | O'Reagan et al. | |
| 2007/0088262 A1 | 4/2007 | Jones et al. | |
| 2007/0093778 A1 | 4/2007 | Cindrich et al. | |
| 2007/0191777 A1 | 8/2007 | King | |
| 2007/0225648 A1 | 9/2007 | Winsor et al. | |
| 2007/0233007 A1 | 10/2007 | Adams | |
| 2007/0270758 A1 | 11/2007 | Hanner | |
| 2008/0039796 A1 | 2/2008 | Nakajima | |
| 2008/0103449 A1 | 5/2008 | Murashita et al. | |
| 2008/0108944 A1 | 5/2008 | Woehr et al. | |
| 2008/0132832 A1 | 6/2008 | McKinnon et al. | |
| 2008/0167577 A1 | 7/2008 | Weilbacher et al. | |
| 2008/0255473 A1 | 10/2008 | Dalebout et al. | |
| 2008/0287906 A1 | 11/2008 | Burkholz et al. | |
| 2009/0054845 A1 | 2/2009 | Puhasmagi et al. | |
| 2009/0099431 A1 | 4/2009 | Dalebout et al. | |
| 2009/0287189 A1 | 11/2009 | Suwito | |
| 2010/0168675 A1 * | 7/2010 | Cindrich | A61M 25/0606 604/167.02 |
| 2010/0168827 A1 * | 7/2010 | Schultz | A61M 25/0136 607/116 |
| 2010/0204648 A1 * | 8/2010 | Stout | A61M 39/0208 604/122 |
| 2010/0204652 A1 * | 8/2010 | Morrissey | A61M 25/0606 604/164.08 |
| 2010/0204675 A1 | 8/2010 | Woehr et al. | |
| 2010/0222746 A1 | 9/2010 | Burkholz | |
| 2010/0280455 A1 | 11/2010 | Ogawa et al. | |
| 2011/0046570 A1 | 2/2011 | Stout et al. | |
| 2011/0054403 A1 | 3/2011 | Tanabe et al. | |
| 2011/0130728 A1 | 6/2011 | McKinnon | |
| 2012/0016265 A1 | 1/2012 | Peterson et al. | |
| 2012/0016307 A1 | 1/2012 | Burkholz et al. | |
| 2012/0053523 A1 | 3/2012 | Harding | |
| 2013/0090608 A1 | 4/2013 | Stout et al. | |
| 2013/0150793 A1 | 6/2013 | Beissel et al. | |
| 2013/0218082 A1 | 8/2013 | Hyer et al. | |
| 2013/0237925 A1 | 9/2013 | Trainer et al. | |
| 2014/0046258 A1 | 2/2014 | Stout et al. | |
| 2014/0107584 A1 | 4/2014 | Rosenberg et al. | |
| 2014/0364809 A1 | 12/2014 | Isaacson et al. | |
| 2015/0224296 A1 | 8/2015 | Winsor | |
| 2017/0080205 A1 * | 3/2017 | Lauer | A61M 39/24 |
| 2017/0120008 A1 | 5/2017 | Burkholz et al. | |
| 2017/0120009 A1 | 5/2017 | Garrison | |
| 2017/0120014 A1 | 5/2017 | Harding et al. | |

(56) References Cited

U.S. PATENT DOCUMENTS

| | | | |
|---|---|---|---|
| 2017/0216535 A1 | 8/2017 | Mao | |
| 2017/0347913 A1 | 12/2017 | Isaacson et al. | |

FOREIGN PATENT DOCUMENTS

| | | | | |
|---|---|---|---|---|
| CN | 101010113 | | 8/2007 | |
| CN | 101296720 | | 10/2008 | |
| CN | 101321549 | | 12/2008 | |
| CN | 101448543 | | 6/2009 | |
| CN | 101879341 | | 11/2010 | |
| CN | 201798996 | | 4/2011 | |
| CN | 102143774 | | 8/2011 | |
| CN | 102355924 | | 2/2012 | |
| CN | 102440822 | | 5/2012 | |
| CN | 102716541 | | 10/2012 | |
| CN | 102802716 | | 11/2012 | |
| CN | 103068434 | | 4/2013 | |
| CN | 206652049 U | | 11/2017 | |
| CN | 206652048 U | | 11/2018 | |
| DE | 3834600 C1 | * | 12/1989 | ........ A61M 39/0613 |
| DE | 202009009602 | | 12/2009 | |
| EP | 139872 A1 | | 5/1985 | |
| EP | 268480 | | 5/1988 | |
| EP | 732120 | | 9/1996 | |
| EP | 812601 | | 12/1997 | |
| EP | 0993839 | | 4/2000 | |
| EP | 1016429 | | 7/2000 | |
| EP | 1306097 | | 5/2003 | |
| EP | 1679043 | | 7/2006 | |
| EP | 1884257 | | 2/2008 | |
| EP | 1944049 | | 7/2008 | |
| EP | 2022421 | | 2/2009 | |
| EP | 2044970 | | 4/2009 | |
| EP | 2327434 | | 6/2011 | |
| EP | 3368118 A2 | | 9/2018 | |
| EP | 3368127 | | 7/2020 | |
| GB | 1506449 A | * | 4/1978 | ....... A61B 5/150732 |
| GB | 2508466 | | 6/2014 | |
| JP | S5464886 | | 5/1979 | |
| JP | S56102253 | | 8/1981 | |
| JP | S5832774 | | 2/1983 | |
| JP | S61-253073 | | 11/1986 | |
| JP | H06-086821 | | 3/1994 | |
| JP | H07-501961 | | 3/1995 | |
| JP | H08257129 | | 10/1996 | |
| JP | H09-509075 | | 9/1997 | |
| JP | 2000279527 | | 10/2000 | |
| JP | 2001-514943 | | 9/2001 | |
| JP | 2004528127 | | 9/2004 | |
| JP | 2005-523782 | | 8/2005 | |
| JP | 2005-526526 | | 9/2005 | |
| JP | 2006019580 | | 1/2006 | |
| JP | 2006019580 A | * | 1/2006 | ........... H02G 15/113 |
| JP | 2008-97955 | | 4/2006 | |
| JP | 2011045544 | | 3/2011 | |
| JP | 2012521796 | | 9/2012 | |
| JP | 2012521797 | | 9/2012 | |
| JP | 2012200425 | | 10/2012 | |
| JP | 3188771 | | 1/2014 | |
| JP | 2018-532012 | | 11/2018 | |
| MX | 2018004611 A | | 8/2018 | |
| WO | 88/07388 | | 10/1988 | |
| WO | 97/45151 | | 12/1997 | |
| WO | 98/42393 | | 10/1998 | |
| WO | 99/34849 | | 7/1999 | |
| WO | 01/12254 | | 2/2001 | |
| WO | 02/096494 | | 12/2001 | |
| WO | 02/096495 | | 12/2002 | |
| WO | 2004/032995 | | 4/2004 | |
| WO | 2004/082727 | | 9/2004 | |
| WO | 2004/087247 | | 10/2004 | |
| WO | 2004/098685 | | 11/2004 | |
| WO | 2006/027923 | | 3/2006 | |
| WO | 2006/037638 | | 4/2006 | |
| WO | 2007/052655 | | 5/2007 | |
| WO | 2008/022258 | | 2/2008 | |
| WO | 2008/045761 | | 4/2008 | |
| WO | 2008/052790 | | 5/2008 | |
| WO | 2008/058132 | | 5/2008 | |
| WO | 2008/058133 | | 5/2008 | |
| WO | 2009/114833 | | 9/2009 | |
| WO | 2010/093791 | | 8/2010 | |
| WO | 2010/111283 | | 9/2010 | |
| WO | 2010/111285 | | 9/2010 | |
| WO | 2011/055287 | | 5/2011 | |
| WO | 2011/109542 | | 9/2011 | |
| WO | 2012/020633 | | 2/2012 | |
| WO | 2015/161299 | | 10/2015 | |
| WO | 2016/152169 | | 9/2016 | |
| WO | 2017074685 A3 | | 5/2017 | |

OTHER PUBLICATIONS

English translation of JP-2006019580-A (Year: 2006).*
Silva, Elson, Email Regarding "Respecting Hydrology Science and IP Rights—US Pat. Application 20110130728," pp. 1-6 (Jun. 2, 2011).

* cited by examiner

SEPTUM HOUSING

CROSS-REFERENCE TO RELATED APPLICATIONS

This application is a divisional of U.S. patent application Ser. No. 15/286,278, filed Oct. 5, 2016, entitled SEPTUM HOUSING, which is incorporated herein in its entirety.

BACKGROUND OF THE INVENTION

Generally, vascular access devices may be used for communicating fluid with a vascular system of a patient. For example, catheter assemblies may be used for infusing fluid, such as normal saline solution, various medications, and total parenteral nutrition, into a patient, withdrawing blood from a patient, or monitoring various parameters of the vascular system of the patient.

A common type of intravenous (IV) catheter is an over-the-needle peripheral IV catheter. As its name implies, an over-the-needle catheter may be mounted over an introducer needle having a sharp distal tip. At least the inner surface of the distal portion of the catheter tightly may engage the outer surface of the needle to prevent peelback of the catheter and thus facilitate insertion of the catheter into the blood vessel. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into a blood vessel.

In order to verify proper placement of the needle and/or catheter in the blood vessel, the clinician generally confirms that there is "flashback" of blood in a flashback chamber of the catheter assembly. Once placement of the needle has been confirmed, the clinician may temporarily occlude flow in the blood vessel at the catheter tip, remove the needle, leaving the catheter in place, and attach a device to the catheter assembly for fluid removal, input, or to seal the catheter assembly. This process has been somewhat difficult in practice since many placement sites simply do not allow easy occlusion of the target vessel. Additionally, even when such occlusion is achieved, it may be imperfect, thus resulting in blood leaking from the catheter assembly, endangering the medical personnel employing it.

Catheter and introducer needle assemblies have thus been provided in the art that provide a variety of seals or "septa" for preventing outflow of fluid during and following removal of the introducer needle. Septum dislodgement is often likely to result in fluid leakage. Septum dislodgement and fluid leakage from an IV catheter assembly may occur due to various circumstances. For example, fluid leakage may occur due to pressurization of the system, which may result from venous pressure, fluid injection under high or low pressure, flush of the system, blood collection, etc.

BRIEF SUMMARY OF THE INVENTION

The present application relates to generally to securement of a septum within a catheter assembly to prevent leakage of fluid from the catheter assembly, as well as related systems and methods. In some embodiments, the catheter assembly may include one or more of the following: a catheter, a catheter adapter, a septum housing, and a septum. In some embodiments, the septum may be at least partially disposed within the septum housing and configured to at least substantially seal a lumen of the catheter adapter. In some embodiments, the septum housing may prevent dislodgement or destabilization of the septum, thereby preventing leakage of fluid from the catheter adapter.

In some embodiments, the catheter assembly may be part of a closed IV catheter system, such as, for example, the BD NEXIVA™ Closed IV Catheter System or the BD NEXIVA™ DIFFUSICS™ Closed IV Catheter System. In the closed IV catheter system, an introducer needle may be withdrawn through the catheter adapter after insertion of the catheter into a blood vessel of a patient. When the introducer needle is withdrawn through the catheter adapter, a "needle channel" may be closed off from an external environment surrounding the catheter system. Further, a side port of the catheter adapter may be connectable to blood withdrawal or infusion means via an extension tube that may extend from the side port of the catheter adapter and may be in fluid communication with the lumen of the catheter adapter. In some embodiments, the septum and/or the septum housing may be disposed proximal to the side port of the catheter adapter.

In some embodiments, the catheter assembly may be part of another type of catheter system. In some embodiments, the catheter adapter may include a distal end, a proximal end, an inner wall extending between the distal end and the proximal end, and a lumen formed by the inner wall. In some embodiments, the septum housing may be disposed within the lumen of the catheter adapter. In some embodiments, the septum housing may include one or more protrusions. In some embodiments, the one or more protrusions may include a lip. In some embodiments, the septum housing may be secured to the inner wall of the catheter adapter by one or more of the following: an interference fit between the one or more protrusions and the inner wall, a snap fit between the one or more protrusions and the inner wall, bonding between the one or more protrusions and the inner wall, and threading securing the one or more protrusions to the inner wall.

In some embodiments, the inner wall may include a groove or opening. In some embodiments, the septum housing may be resilient, and in response to the one or more protrusions aligning with the groove or opening, the septum housing may resiliently move outward to retain the one or more protrusions within the groove or opening in the snap fit. In further detail, in some embodiments, in response to the septum housing being inserted into the distal end of the catheter adapter, the one or more protrusions may be biased inwardly and/or in response to the one or more protrusions being further inserted into the distal end and aligning with the groove or opening, the one or more protrusions move resiliently outward such that the one or more protrusions are retained in the groove or opening.

In some embodiments, the bonding between the one or more protrusions and the inner wall may include adhesive bonding. Additionally or alternatively, in some embodiments, the bonding between the one or more protrusions and the inner wall may include chemical bonding. Additionally or alternatively, in some embodiments, the bonding between the one or more protrusions and the inner wall may include ultrasonic welding. Additionally or alternatively, in some embodiments, the bonding between the one or more protrusions and the inner wall may include laser welding. Additionally or alternatively, the one or more protrusions may include one or more threads, which may be disposed on a distal end of the septum housing. In some embodiments, the inner wall of the catheter adapter may include corresponding threads to secure the septum housing to the inner wall.

In some embodiments, the lip may extend around all or a portion of a circumference of the septum housing. In some embodiments, the lip may be disposed at a distal end of the septum housing. In some embodiments, the adhesive bonding and/or the chemical bonding may extend along an exterior of the septum housing proximal to the lip. In some embodiments, the inner wall may include a ring that contacts the exterior of the septum housing proximal to the lip such that a cavity is formed between the ring and the lip. In some embodiments, the cavity may extend around an outer circumference of the septum housing and/or an inner circumference of the catheter adapter. In some embodiments, the cavity may secure the adhesive bonding and/or the chemical bonding.

In some embodiments, the catheter adapter may include a vent hole that provides a venting pathway between an exterior of the catheter assembly and the adhesive bonding and/or the chemical bonding. In some embodiments, the vent hole and the venting pathway may be used to access the catheter adapter to introduce the adhesive bonding and/or the chemical bonding into the catheter adapter. In some embodiments, the venting pathway may provide access and/or venting to the cavity. In some embodiments, the cavity may include an angled proximal surface, which may facilitate spreading of the adhesive bonding and/or the chemical bonding through the cavity and around the outer circumference of the septum housing.

In some embodiments, the bonding between the septum housing and the inner wall and/or between the septum and the inner wall may be disposed at various locations on the inner wall. In some embodiments, one or more of the following: adhesive bonding, chemical bonding, ultrasonic welding, and laser welding, may be disposed on all or some surfaces of the inner wall and/or the septum that are in contact. Additionally or alternatively, one or more of the following: adhesive bonding, chemical bonding, ultrasonic welding, and laser welding, may be disposed on all or some surfaces of the inner wall and/or the septum housing that are in contact. In some embodiments, the vent hole may be disposed at various locations within the catheter adapter to provide access to the catheter adapter and/or a venting pathway between the exterior of the catheter assembly and particular adhesive bonding and/or particular chemical bonding. In some embodiments, the vent hole may be disposed proximate to a proximal edge of the lip. In some embodiments, the catheter adapter may comprise a vent hole, and may further comprise port through which the adhesive or chemical bonding material is injected, wherein the vent hole prevents pressure buildup between the septum and/or the septum housing and the inner wall of the catheter adapter during the injection adhesive or chemical bonding material.

In some embodiments, the one or more protrusions of the septum housing may each include a resilient catch feature. In some embodiments, multiple catch features may be spaced apart about an outer circumference of the septum housing. In some embodiments, an exterior of the catheter adapter may include a safety mechanism engagement feature. In some embodiments, the safety mechanism engagement feature may be spaced apart from the opening in the inner wall. In some embodiments, the safety engagement feature may include a groove configured to selectively couple with a V-clip or similar clip. In some embodiments, the safety engagement feature may be spaced apart from the opening in the inner wall of the catheter adapter.

In some embodiments, the septum may be housed and retained within the catheter adapter without requiring a mechanical or interference interface with the septum housing. For example, the proximal end of the catheter adapter may abut and extend over a portion of a surface area of a proximal face of the septum, thereby retaining the septum within the catheter adapter. Thus, the catheter adapter may prevent the septum from moving proximally within the catheter adapter due to a wall at the proximal end of the catheter adapter that abuts and thereby partially blocks the proximal end of the catheter adapter.

In these and other embodiments, the catheter adapter may include at least two pieces. In some embodiments, the catheter adapter may include a proximal piece, a distal piece, and a lumen extending through the proximal piece and the distal piece. In some embodiments, the proximal piece and the distal piece may be selectively coupled together at a coupling. In some embodiments, the distal piece may include the side port. In some embodiments, the proximal piece may be disposed proximal to the side port. In some embodiments, the proximal and distal pieces may facilitate insertion of the septum into the catheter adapter given the proximal end of the catheter adapter may not include an opening large enough to fit the septum.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1A:
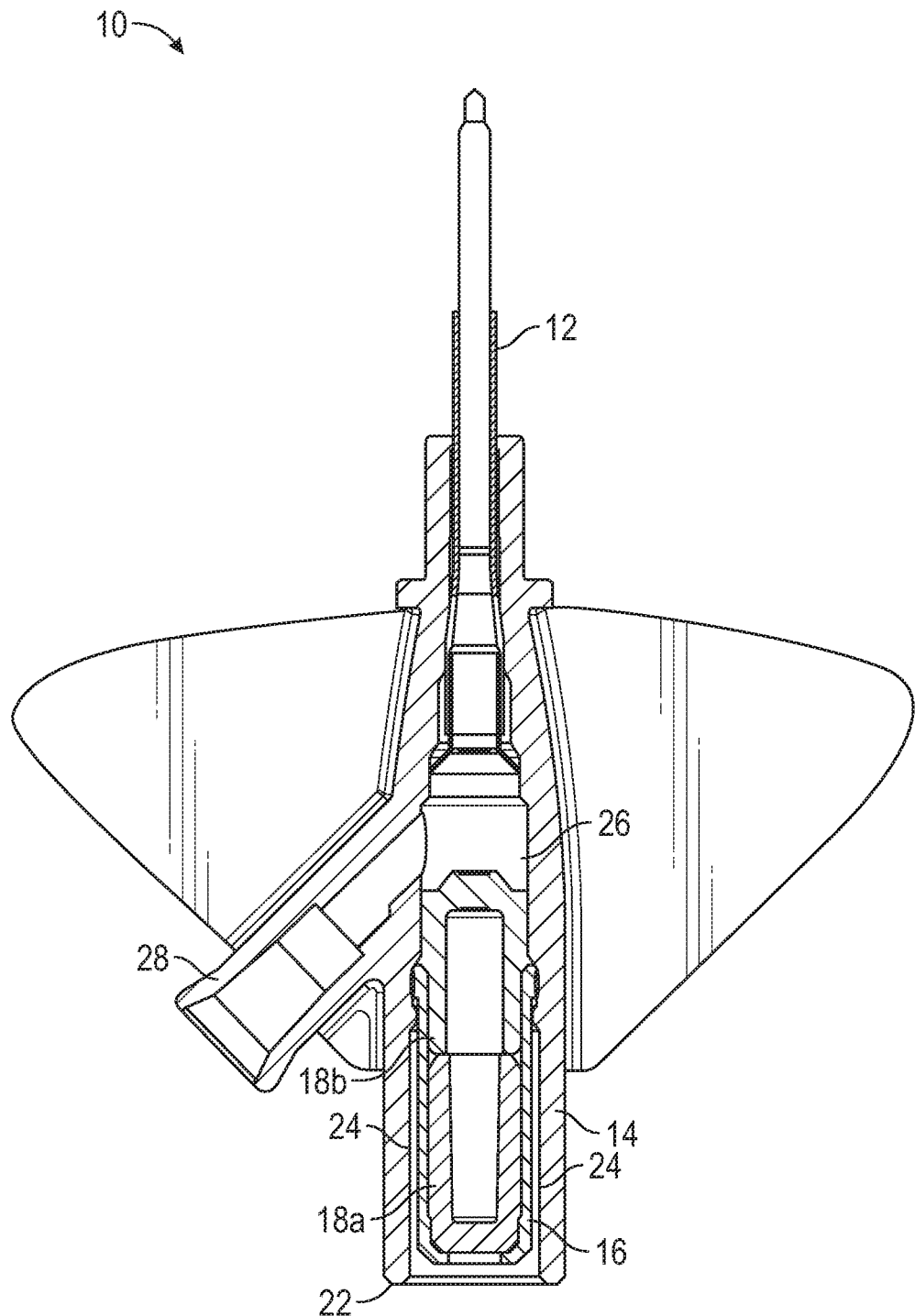
FIG. 1A is a cross-sectional top view of an example catheter assembly, according to some embodiments.

Referring now to FIG. 1A, in some embodiments, a catheter assembly 10 may include one or more of the following: a catheter 12, a catheter adapter 14, a septum housing 16, and a septum 18. In some embodiments, the catheter adapter 14 may include a distal end 20, a proximal end 22, an inner wall 24 extending between the distal end 20 and the proximal end 22, and a lumen 26 formed by the inner wall 24. In some embodiments, the septum housing 16 may be disposed within the lumen 26 of the catheter adapter 14.

In some embodiments, the septum 18 may be at least partially disposed within the septum housing 16 and configured to at least substantially seal the proximal end 22 and/or a lumen of the catheter adapter 14. In some embodiments, the septum housing 16 may prevent dislodgement or destabilization of the septum 18, thereby preventing leakage of fluid from the catheter adapter.

In some embodiments, the catheter assembly 10 may be part of a closed IV catheter system, such as, for example, the BD NEXIVA™ Closed IV Catheter System, the BD NEXIVA™ DIFFUSICS™ Closed IV Catheter System, the BD Intima II™ Catheter, or similar catheter systems. In some embodiments, the catheter assembly 10 may be part of another type of catheter system. In the closed IV catheter system, an introducer needle (not illustrated in FIG. 1A) may be withdrawn through the catheter adapter 14 after insertion of the catheter 12 into a blood vessel of a patient. When the introducer needle is withdrawn through the catheter adapter 14, a "needle channel" may be closed off from an external environment surrounding the catheter assembly 10. Further, a side port 28 of the catheter adapter 14 may be connectable to blood withdrawal or infusion means via an extension tube that may extend from the side port 28 of the catheter adapter 14 and may be in fluid communication with the lumen 26 of the catheter adapter 14. In some embodiments, the septum 18 and/or the septum housing 16 may be disposed proximal to the side port 28 of the catheter adapter 14.

Figure 1B:
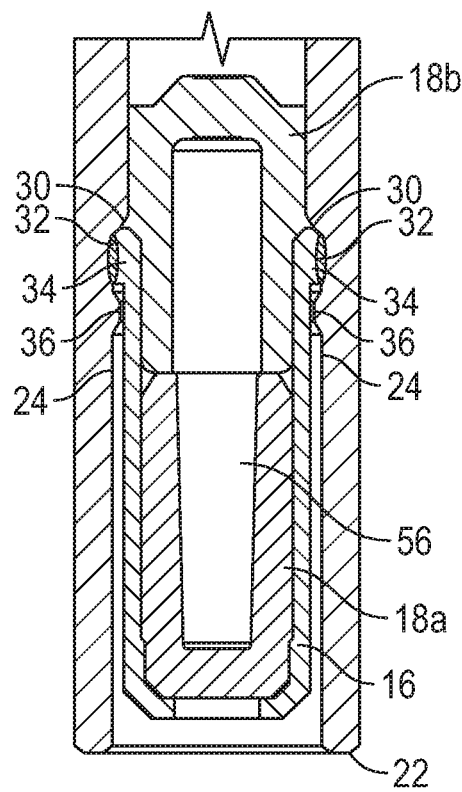
FIG. 1B is an enlarged cross-sectional top view of a portion of the catheter assembly of FIG. 1A, illustrating example ultrasonic welding, according to some embodiments.

Referring now to FIG. 1B, in some embodiments, the septum housing 16 may include one or more protrusions. In some embodiments, the septum housing may be secured to the inner wall 24 of the catheter adapter 14 by one or more of the following: an interference fit between the one or more protrusions and the inner wall 24, a snap fit between the one or more protrusions and the inner wall 24, and bonding between the one or more protrusions and the inner wall 24.

Figure 4A:
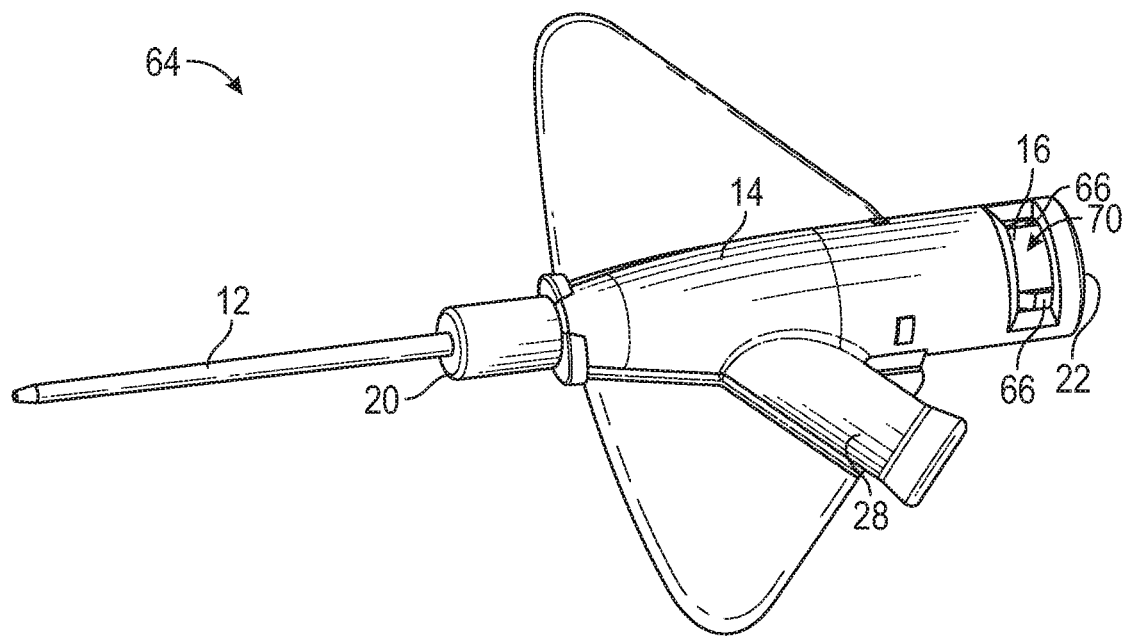
FIG. 4A is a top view of another example catheter assembly, according to some embodiments.
Figure 4B:
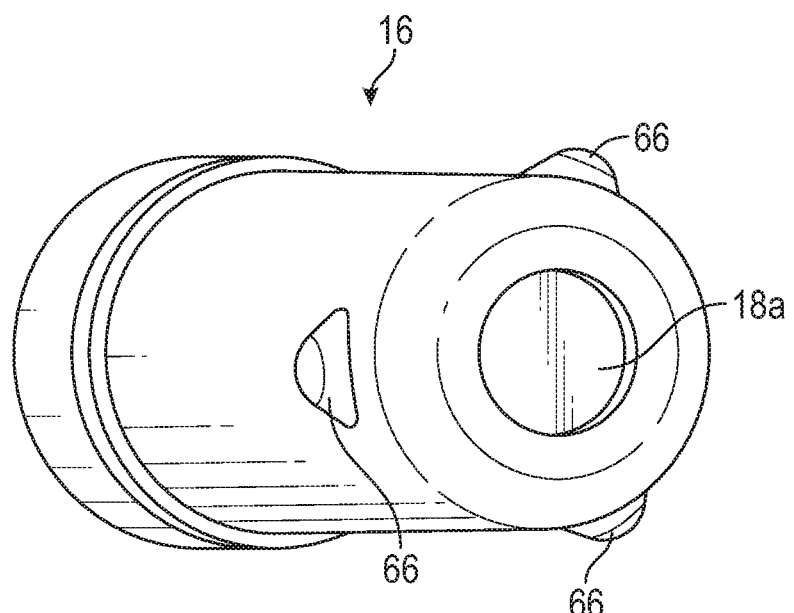
FIG. 4B is an upper perspective view of an example septum housing, according to some embodiments.
Figure 4C:
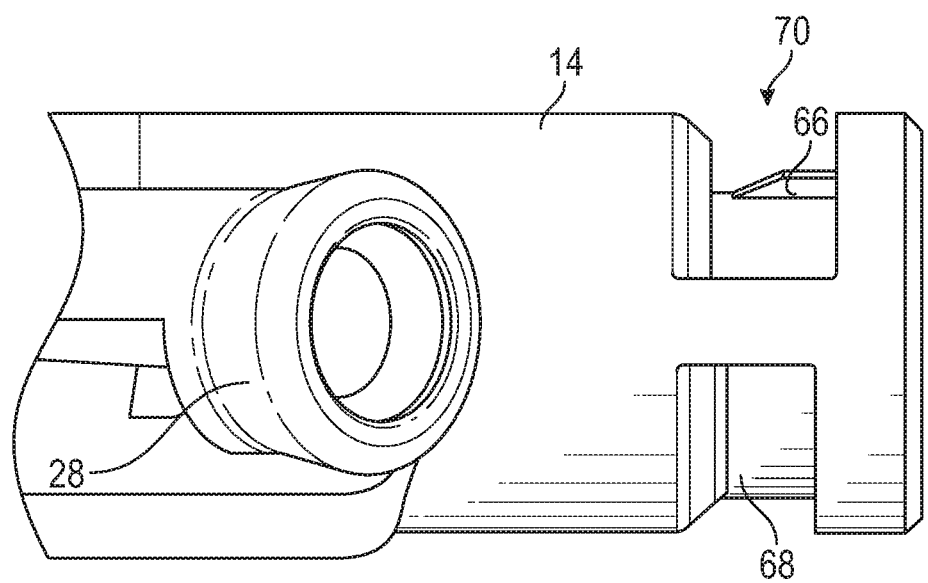
FIG. 4C is a side view of a portion of the catheter assembly of FIG. 4A, according to some embodiments.
Figure 4D:
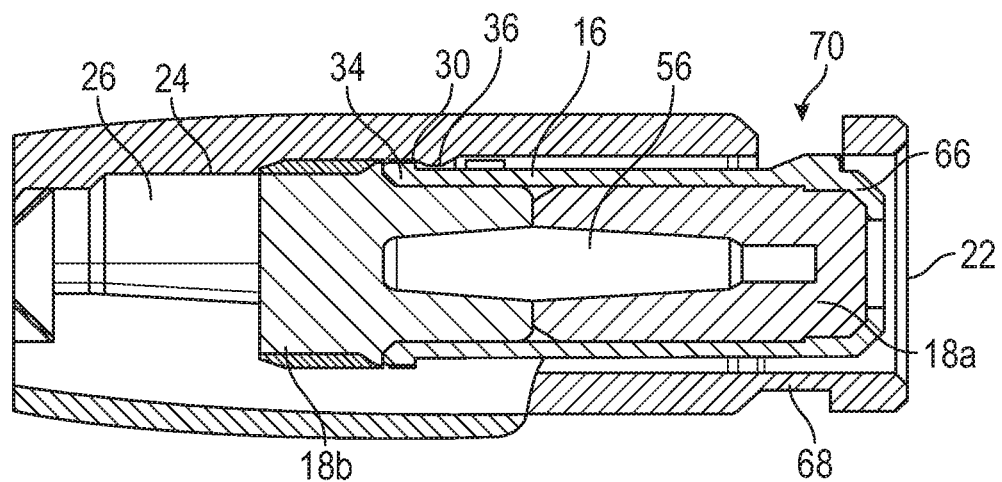
FIG. 4D is a cross-sectional view of the portion of the catheter assembly of FIG. 4C, according to some embodiments.
Figure 4E:
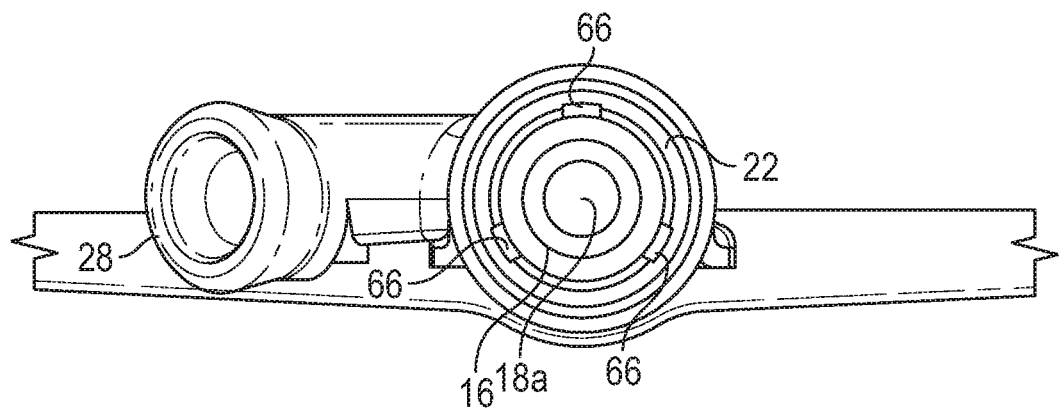
FIG. 4E is a proximal view of the catheter assembly of FIG. 4A, according to some embodiments.

In some embodiments, the inner wall 24 may include a groove 30 or opening (an example opening 70 is illustrated in FIGS. 4A and 4C-4D). It is understood that the inner wall 24 may include multiple grooves 30 and/or multiple openings and that each of the multiple grooves and/or the multiple openings may be configured to retain one or more of the protrusions. In some embodiments, the septum housing 16 may be resilient, and in response to the one or more protrusions aligning with the groove 30 or opening, the septum housing 16 may resiliently move outward to retain the one or more protrusions within the groove 30 or opening in the snap fit. In further detail, in some embodiments, in response to the septum housing 16 being inserted into the proximal end 22 of the catheter adapter 14, the one or more protrusions may be biased inwardly and/or in response to the one or more protrusions being further inserted into the proximal end 22 and aligning with the groove 30 or opening, the one or more protrusions move resiliently outward such that the one or more protrusions are retained within the groove 30 or opening.

In some embodiments, when the one or more protrusions are aligned with the groove 30 in the snap fit, the one or more protrusions may be disposed in an interference fit with the groove 30. As interference between the septum housing 16 and the catheter adapter 14 increases, there may be an increased probability and/or severity of deformation of the septum 18 and/or other components of the catheter assembly 10. As interference between the septum housing 16 and the catheter adapter 14 increases, there may also be an increased likelihood of stress-induced crazing of the septum housing 16, the catheter adapter 14 and/or other components of the catheter assembly 10. In some embodiments, the interference fit between the one or more protrusions and the groove 30 may facilitate avoidance of the deformation and/or the stress-induced crazing while still providing support against dislodgement or destabilization of the septum 18. In some embodiments, a lubricant, such as, for example, alcohol or silicone, may be used for uniform seating of the septum within the septum housing 16 and/or the catheter adapter 14. The lubricant may also reduce stress-induced crazing. The lubricant may also increase a maximum pressure performance, which may include a maximum amount of pressure that can be applied to the septum 18 and/or the septum housing 16 without significant dislodgement of the septum 18 as the introducer needle is withdrawn. In some embodiments, an alcohol lubricant may increase the maximum pressure performance more than a silicone lubricant.

In some embodiments, the one or more protrusions of the septum housing may include a lip 34. In some embodiments, the lip 34 may extend around all or a portion of a circumference of the septum housing 16. In some embodiments, the lip 34 may be disposed at a distal end of the septum housing 16. In some embodiments, the interference fit between the lip 34 and the groove 30 may be tighter due to the lip 34 being enlarged. An enlarged size of the lip 34 may increase the maximum pressure performance. In some embodiments, the lip 34 may provide better interference and greater maximum pressure performance than multiple protrusions, which may be spaced apart and not extend around an entire circumference of the septum housing 16.

In some embodiments, the bonding between the one or more protrusions and the inner wall may include ultrasonic welding 32. In some embodiments, the ultrasonic welding 32 may increase the maximum pressure performance. In some embodiments, laser welding may be used instead of or in addition to the ultrasonic welding 32. In some embodiments, a premixed resin or colorant may be applied in a location of the laser welding and/or the ultrasonic welding 32, which may create uniform transmissivity resulting in more consistent weld performance.

In some embodiments, the laser welding and/or the ultrasonic welding 32 may be configured not to fail a minimum threshold energy to facilitate adhesion or a maximum threshold energy to avoid damaging any components of the catheter assembly 10, such as, for example, the septum 18, the septum housing 16, and the catheter adapter 14.

In some embodiments, the bonding between the septum housing 16 and the inner wall 24 and/or between the septum 18 and the inner wall 24 may be disposed at various locations on the inner wall 24. In some embodiments, the ultrasonic welding 32 may be disposed where the inner wall 24 contacts the septum 18 and/or the septum housing 16. In some embodiments, the inner wall 24 may include one or more other protrusions or a ring 36. In some embodiments, the one or more other protrusions or the ring 36 may form a proximal edge of the groove 30. In some embodiments, the ultrasonic welding 32 may be disposed between the one or more other protrusions or the ring 36 and an external surface of the septum housing 16, as illustrated in FIG. 1B.

Figure 1C:
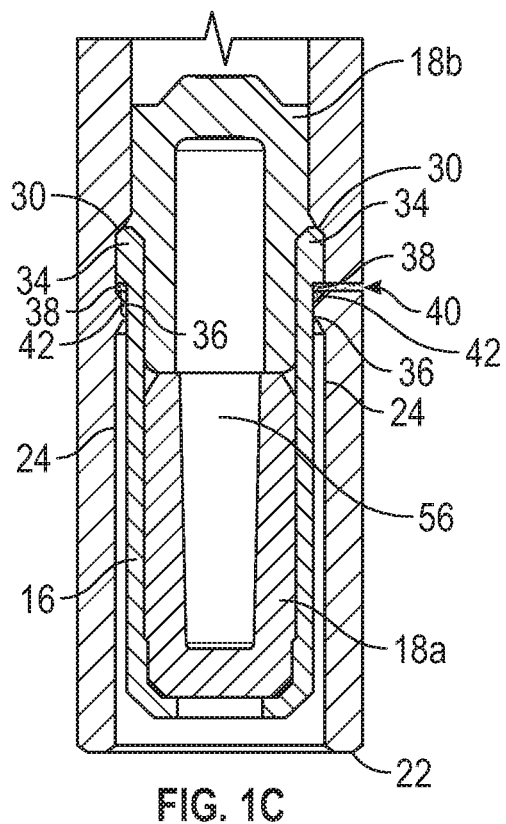
FIG. 1C is an enlarged cross-sectional top view of the portion of the catheter assembly of FIG. 1B, illustrating example adhesive bonding, according to some embodiments.

Referring now to FIG. 1C, in some embodiments, the bonding between the one or more protrusions and the inner wall 24 may include adhesive bonding 38. In some embodiments, the adhesive bonding 38 may include glue or another adhesive. In some embodiments, the adhesive bonding 38 may extend along an exterior of the septum housing 16 proximal to the lip 34. In some embodiments, the ring 36 may contact the exterior of the septum housing 16 proximal to the lip 34 such that a cavity is formed between the ring 36 and the lip 34. In some embodiments, the cavity may extend around an outer circumference of the septum housing 16 and/or an inner circumference of the catheter adapter 14. In some embodiments, the multiple cavities may be formed between the one or more protrusions of the septum housing 16 and the one or more other protrusions of the catheter adapter 14.

Figure 1D:
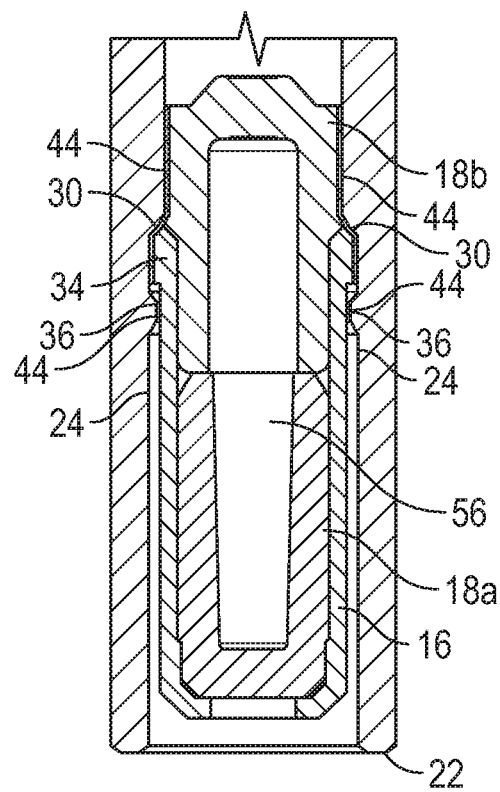
FIG. 1D is an enlarged cross-sectional top view of the portion of the catheter assembly of FIG. 1B, illustrating example chemical bonding, according to some embodiments.

In some embodiments, the catheter adapter 14 may include one or more vent holes 40 that provide venting pathways between an exterior environment of the catheter assembly 10 and the adhesive bonding 38 and/or the chemical bonding (illustrated in FIG. 1D). In some embodiments, the vent holes 40 and their corresponding venting pathways may be used to access the catheter adapter 14 to introduce the adhesive bonding 38 and/or the chemical bonding into the catheter adapter 14, such as, for example, into the cavity of the catheter adapter 14. In some embodiments, the venting pathways may each provide access and/or venting to the cavity. In some embodiments, the cavity may include an angled proximal surface 42, which may facilitate spreading of the adhesive bonding 38 and/or the chemical bonding through the cavity and around the outer circumference of the septum housing 16.

In some embodiments, the vent holes 40 may be disposed as various locations within the inner wall 24 of the catheter adapter 14 to provide access to the catheter adapter 14 and/or a venting pathway between the exterior of the catheter assembly 10 and particular adhesive bonding 38 and/or particular chemical bonding. In some embodiments, a particular vent hole 40 may be disposed proximate to a proximal edge of the lip 34.

In some embodiments, the ring 36 may include a retention ring or washer that may be placed around the lip 34 or another portion of the septum housing 16. In some embodiments, the adhesive bonding 38 may be disposed between the retention ring and the inner wall 24.

Referring now to FIG. 1D, in some embodiments, the bonding between the one or more protrusions and the inner wall 24 may include solvent or chemical bonding 44. In some embodiments, the chemical bonding 44 may be disposed where the inner wall 24 contacts the septum 18 and/or the septum housing 16.

Figure 1E:
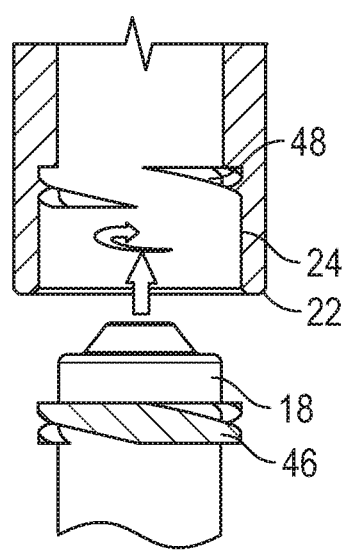
FIG. 1E is a partial cutaway top view of an example threads of the catheter assembly of FIG. 1A, according to some embodiments.

Referring now to FIG. 1E, in some embodiments, the one or more protrusions may include one or more threads 46, which may be disposed on a distal end of the septum housing 16. In some embodiments, the inner wall 24 of the catheter adapter 14 may include corresponding threads 48 to secure the septum housing 16 to the inner wall 24.

Figure 1F:
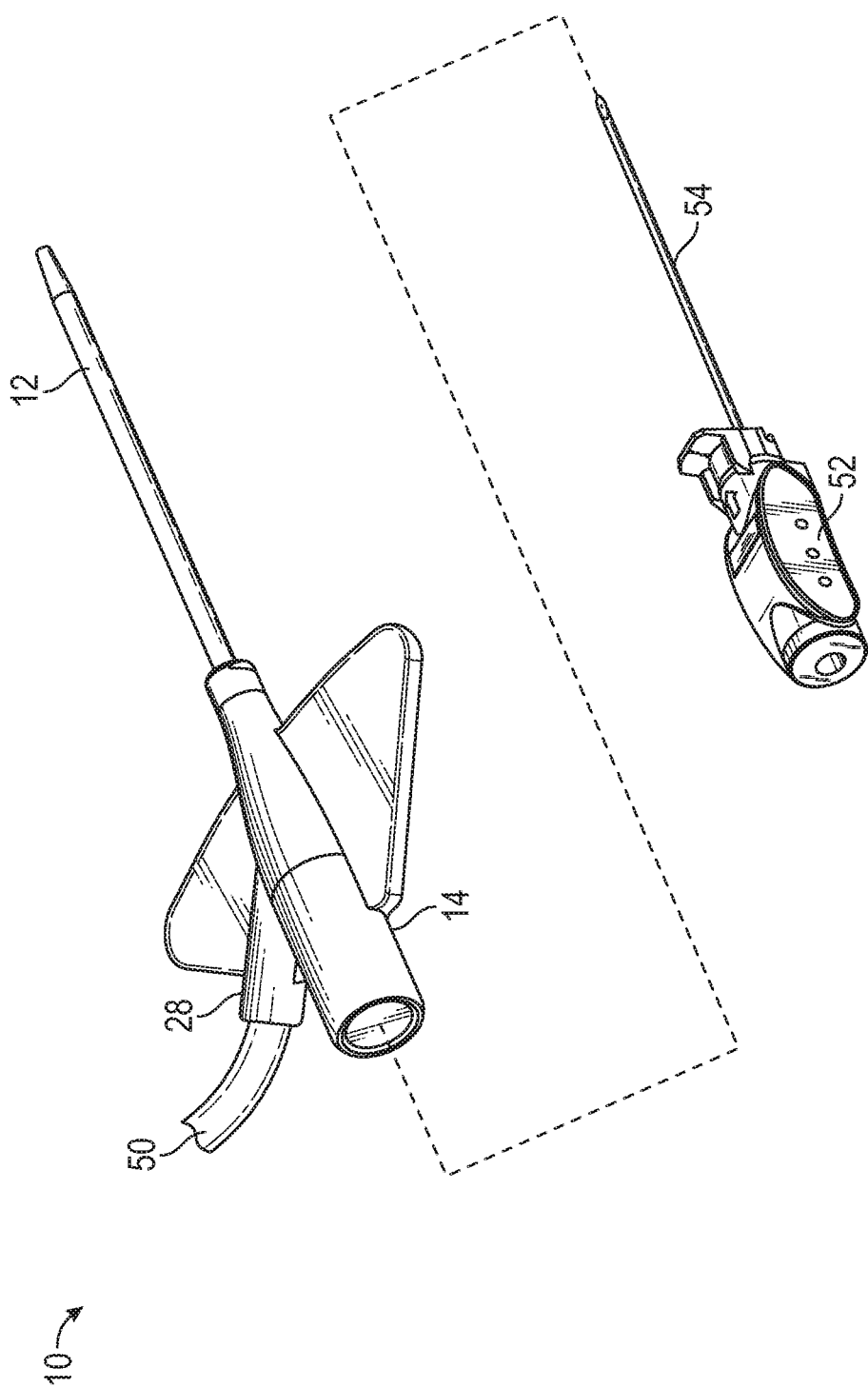
FIG. 1F is a perspective view of the catheter assembly of FIG. 1A, according to some embodiments.

Referring now to FIG. 1F, in some embodiments, an extension tube 50 is connected to the side port 28. In some embodiments, the catheter assembly 10 may include a needle hub 52. In some embodiments, a proximal end of the introducer needle 54 may be connected to the needle hub 52. In some embodiments, the needle hub 52 may include a needle shielding mechanism.

Figure 1G:
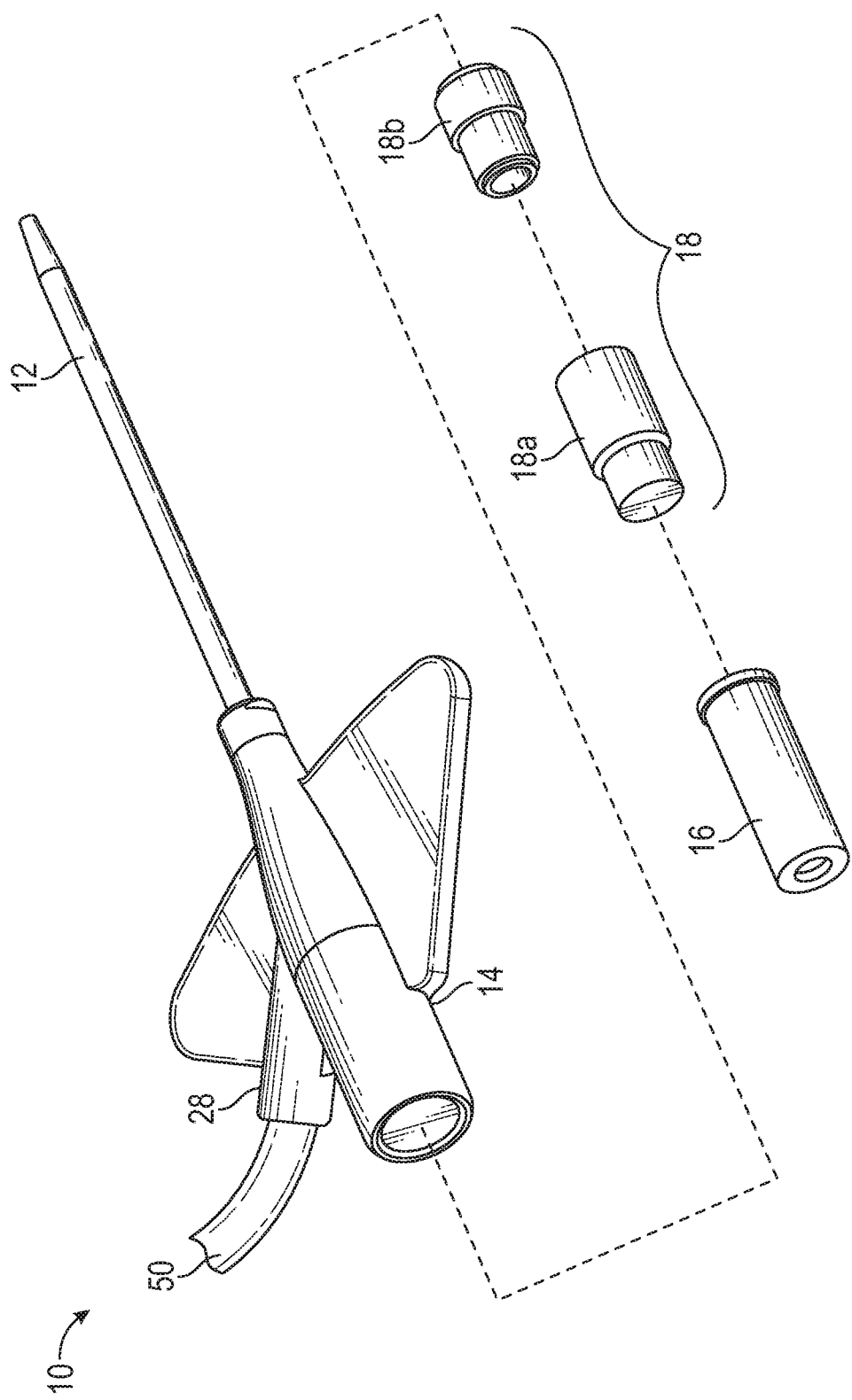
FIG. 1G is an exploded view of the catheter assembly of FIG. 1A, according to some embodiments.

Referring now to FIG. 1G, in some embodiments, the septum 18 may be formed from two portions, a proximal portion 18a and a distal portion 18b. In some embodiments, each of the portions 18a, 18b may be pre-slit to facilitate locating the introducer needle 54 therethrough. Suitable materials for the septum 18 may include a peroxide cured elastomer such as polyisoprene, silicone, and the like where the materials have a durometer in the range of 35-45 Shore A.

In some embodiments, the septum housing 16 may be constructed of a resilient material. Non-limiting examples of resilient material include stainless steel, polyethylene, polypropylene, polycarbonate, polyethylene terephthalate (PET), polyethylene terephthalate glycol-modified (PETG), and polyester. In some embodiments, the catheter adapter 14 may be constructed of a same or similar material as the septum housing 16 to facilitate strength of the bonding between the catheter adapter 14 and the septum housing 16.

In some embodiments, the septum housing 16 may have an open proximal end and an open distal end. In some embodiments, the septum housing 16 may surround at least a portion of the proximal portion 18a and the distal portion 18b in an interference fit to hold the septum 18 in place in position in the catheter adapter 14. In some embodiments, the septum housing 16 may extend along only a portion of the distal portion 18b. However, in some embodiments, the septum housing 16 may extend along an entire length of the septum 18 or just along the proximal portion 18a. In some embodiments, at least a portion of the septum 18 may engage the inner wall 24.

In some embodiments, the septum housing 16 may be configured to apply a compressive force to the septum 18. In some embodiments, the open proximal and distal ends of the septum housing 16 may allow the introducer needle 54 to extend through the septum 18 past the septum housing 16. In some embodiments, the proximal end of the septum housing 16 may abut and extend over a portion of a surface area of a proximal face of the septum 18.

In some embodiments, the septum 18 may be a low-drag septum, which may facilitate stability and uniformity of the septum 18 during insertion of the catheter assembly 10 into the blood vessel of the patient. Referring back to FIG. 1B, in some embodiments, the septum 18 may include a hollow interior portion 56 formed between the proximal portion 18a and the distal portion 18b. The hollow interior portion 56 may minimize drag on introducer needle 54 as it is being withdrawn from catheter assembly 10.

In some embodiments, an external diameter of at least a portion of the distal portion 18b may be greater than an internal diameter of catheter adapter 14. In some embodiments, the external diameter of the distal portion 18b may be at least 5% larger than the internal diameter of the relevant portion of catheter adapter 14. With this configuration, the catheter adapter 14 may exert a radial compressive force against the distal portion 18b. This compressive force may help to hold the septum housing 16 in place.

Although illustrated in FIG. 1G as a low-drag, two-piece septum 18, the septum 18 may include various types of septa. For example, referring now to FIG. 2, in some embodiments, the septum 18 may be formed from one piece. In some embodiments, the one piece septum may be low-drag. In some embodiments, the septum 18 may be self-retaining, for example, the septum 18 may be at least partially retained within the septum housing 16 and/or the catheter adapter 14 by means of an interference or friction fit between the septum 18 and the inner wall 24, a mass of the septum 18, etc.

In some embodiments, the septum housing 58 may include or correspond to the septum housing 16. In some embodiments, a length of the septum housing 58 may be less than a length of the septum housing 16. The septum housing 58 may be secured to the inner wall 24 of the catheter adapter 14 similar to the septum housing 16. For example, the septum housing 58 may be secured to the inner wall 24 by one or more of the following: an interference fit between the one or more protrusions and the inner wall 24, a snap fit between the one or more protrusions and the inner wall 24, and bonding between the one or more protrusions and the inner wall 24.

Figure 2:
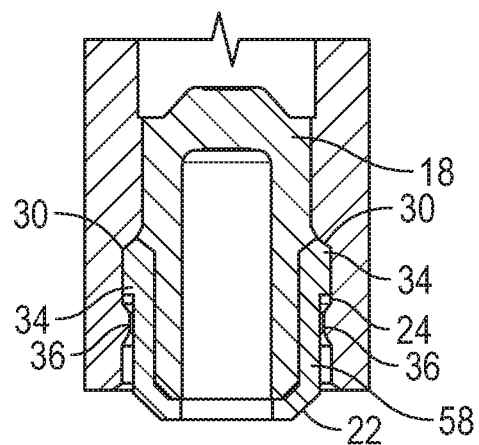
FIG. 2 is a cross-sectional view of an example septum and an example septum housing, according to some embodiments.
Figure 3A:
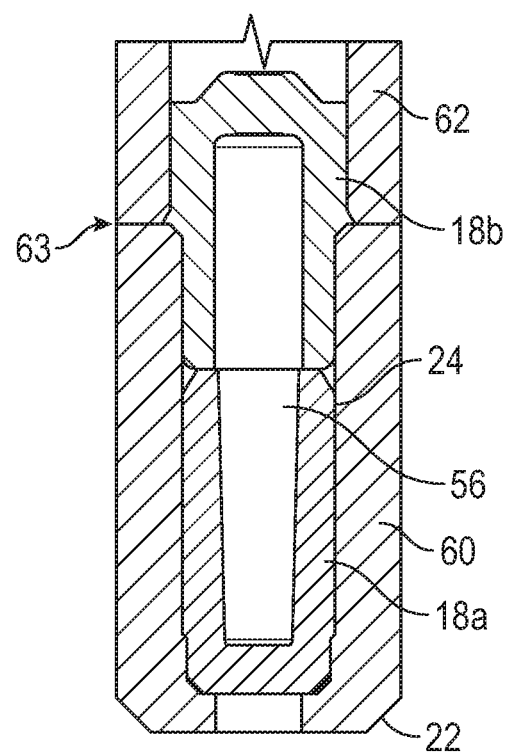
FIG. 3A is a cross-sectional view of the portion of the catheter assembly of FIG. 1B, according to some embodiments.

Referring now to FIG. 3A, in some embodiments, the septum 18 may be housed by the catheter adapter 14 without use of a particular septum housing, such as, for example, the septum housing 16 of FIG. 1 or the septum housing 58 of FIG. 2. For example, the proximal end of the catheter adapter 14 may abut and extend over a portion of a surface area of a proximal face of the septum 18. Thus, the catheter adapter 14 may prevent the septum 18 from moving proximally within the catheter adapter 14 due to a wall at the proximal end of the catheter adapter 14 that abuts the proximal end of the catheter adapter 14.

In some embodiments, the catheter adapter 14 may include at least two pieces. In some embodiments, the catheter adapter 14 may include a proximal piece 60, a distal piece 62, and the lumen 26 extending through the proximal piece 60 and the distal piece 62. In some embodiments, the proximal piece 60 and the distal piece 62 may be selectively coupled together at a coupling 63. In some embodiments, the distal piece 62 may include the side port 28. In some embodiments, the proximal piece 60 may be disposed proximal to the side port 28. In some embodiments, the proximal and distal pieces 60, 62 may facilitate insertion of the septum 18 into the catheter adapter 14 during assembly of the catheter assembly 10 given that the proximal end of the catheter adapter 14 may not include an opening large enough to fit the septum 18.

Figure 3B:
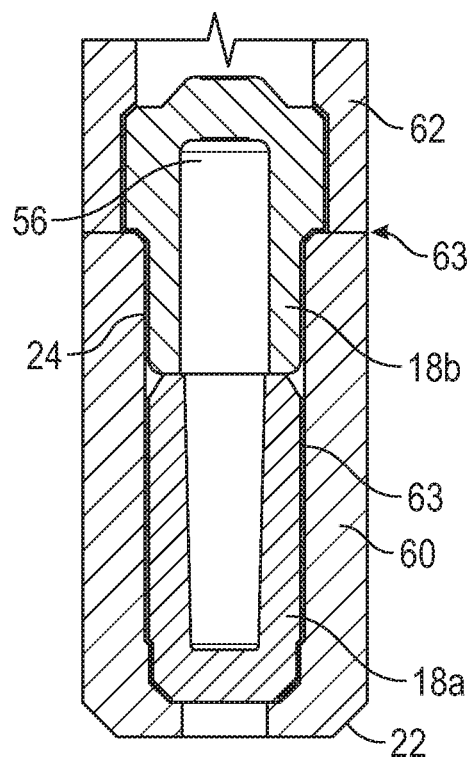
FIG. 3B is a cross-sectional view of the portion of the catheter assembly of FIG. 1B, illustrating example chemical bonding, according to some embodiments.

Referring now to FIG. 3B, in some embodiments, the septum 18 may be secured to the inner wall of the catheter adapter 14 by bonding 65 between the septum 18 and the inner wall. The bonding may include one or more of the following: the adhesive bonding 38 described in the present disclosure, the chemical bonding 44 described in the present disclosure, or another suitable type of bonding. In some embodiments, the bonding may be disposed along at least a portion of a length of the septum 18.

Referring now to FIGS. 4A-4F, in some embodiments, a catheter assembly 64 may include or correspond to the catheter assembly 10. In some embodiments, the one or more protrusions of the septum housing 16 may each include a resilient catch feature 66. In some embodiments, multiple catch features 66 may be spaced apart about an outer circumference of the septum housing 16. In some embodiments, the spacing of the catch features 66 may allow the septum housing 16 to be inserted through a proximal opening in the proximal end 22 without regard to orientation.

Figure 4F:
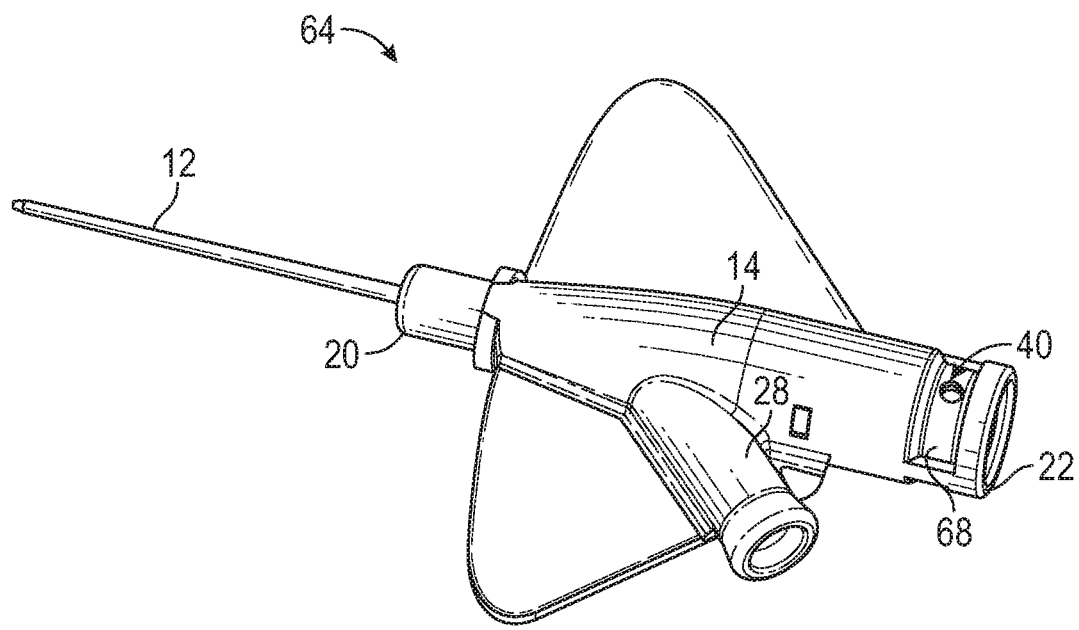
FIG. 4F is a lower perspective view of the catheter assembly of FIG. 4A, illustrating an example safety mechanism securement feature and an example vent hole, according to some embodiments.

In some embodiments, an exterior of the catheter adapter 14 may include a safety mechanism engagement feature 68. In some embodiments, the safety mechanism engagement feature 68 may be spaced apart from the opening 70 in the inner wall 24. In some embodiments, the safety mechanism engagement feature 68 may include a groove configured to selectively couple with a V-clip or similar clip (not illustrated in FIGS. 4A-4F). In some embodiments, the safety mechanism engagement feature 68 may be spaced apart from the opening 70 in the inner wall of the catheter adapter 14. In some embodiments, the safety mechanism engagement feature 68 may be disposed on an opposite side of the catheter adapter 14 as the opening 70. In some embodiments, a particular vent hole 40 may be aligned with and/or disposed within the safety mechanism engagement feature 68, as illustrated in FIG. 4F. Although the septum illustrated in FIGS. 4A-4F is a two-piece septum 18, in some embodiments, a one-piece septum 18 may be used.

Figure 5A:
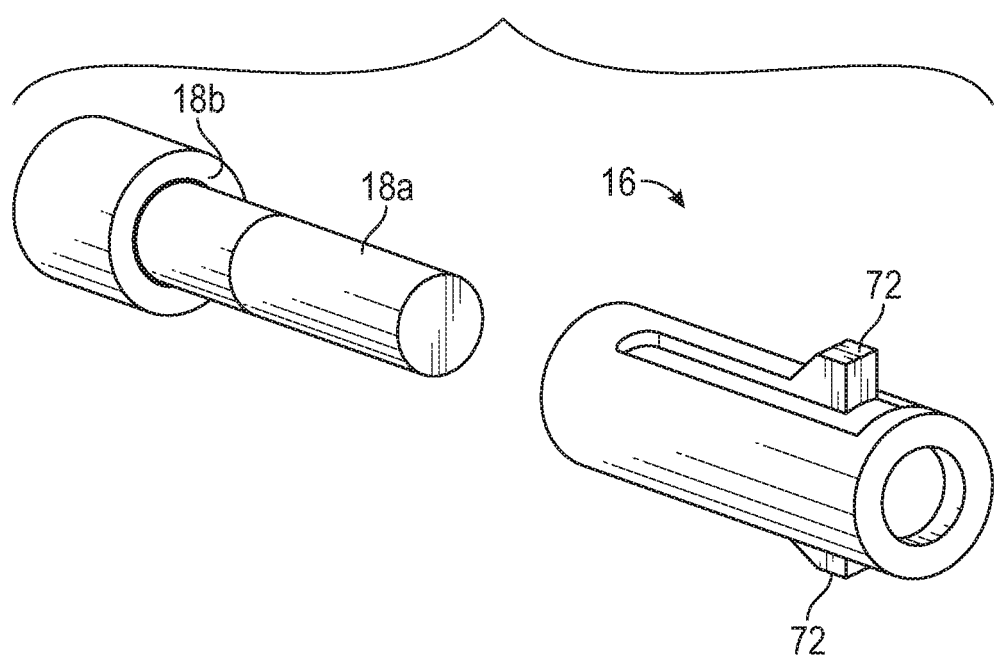
FIG. 5A is an upper perspective view of another example septum housing and example septum, according to some embodiments.
Figure 5B:
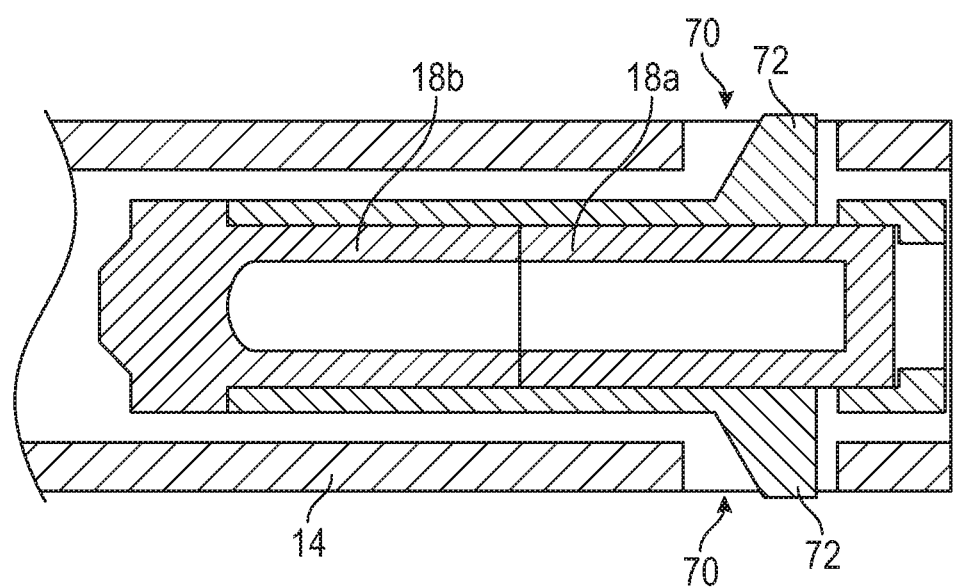
FIG. 5B is a cross-sectional view of the septum housing and the septum of FIG. 5A disposed within an example catheter adapter.

Referring now to FIGS. 5A-5B, in some embodiments, a catheter assembly 71 may include or correspond to the catheter assembly 10 or the catheter assembly 64. As illustrated in FIG. 5A, in some embodiments, the one or more protrusions of the septum housing 16 may include one or more catch features 72 disposed on one or more arms of the septum housing 16, which may be constructed of a resilient material. In some embodiments, the septum housing 16 may include two of the catch features 72, which may be disposed on opposite sides of the septum housing 16. In some embodiments, each of the arms may be connected to a body of the septum housing 16 at a base on the corresponding arm opposite the catch feature 72. In some embodiments, each of the arms may be spaced apart and/or separated from the body of the septum housing 16 along one or both sides of the arm and/or at an end of the arm opposite the base.

In some embodiments, in response to the septum housing 16 being inserted into the distal end of the catheter adapter 14, the catch features 72 and the arms may be biased inwardly. In some embodiments, in response to catch features 72 being further inserted into the distal end and aligning with one or more grooves and/or openings 70, the catch features 72 and arms may move resiliently outward such that the catch features 72 are retained in the grooves and/or the openings 70 in a snap fit.

In some embodiments, the catheter adapter 14 may include any suitable number of grooves or openings 70, which may each be configured to retain one or more of the retention features 72. As illustrated in FIG. 1B, in some embodiments, the catheter adapter 14 may include two openings 70 which may be disposed on opposite sides of the catheter adapter 14. In some embodiments, each of the openings 70 may be configured to retain at least one of the catch features 72.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly, comprising:
    a catheter adapter, wherein the catheter adapter comprises a distal end, a proximal end, an inner wall extending between the distal end and the proximal end, a lumen formed by the inner wall, and a side port, wherein the inner wall comprises a groove;
    a septum housing disposed within the lumen of the catheter adapter, wherein a distalmost end of the septum housing comprises a protrusion, wherein the groove of the inner wall is sized and configured to receive the protrusion in a snap fit, wherein when the protrusion is in the snap fit, the protrusion is disposed in an interference fit with the groove, wherein in response to the septum housing being inserted into the proximal end of the catheter adapter, the protrusion is biased inwardly, wherein in response to the protrusion being further inserted into the proximal end of the catheter adapter and aligning with the groove, the protrusion moves resiliently outward such that the protrusion is retained in the groove in the snap fit; and
    a septum at least partially disposed within the septum housing and proximal to the side port, wherein the septum is configured to at least substantially seal the lumen, wherein the septum comprises a distal piece, a proximal piece, and a hollow interior portion enclosed by the distal piece and the proximal piece, wherein a portion of the distal piece is disposed within the groove and proximate the protrusion;
    wherein the septum housing is secured to the inner wall by bonding between the protrusion on the distal end of the septum housing and the inner wall of the lumen of the catheter adapter;
    wherein the bonding comprises laser or ultrasonic welding.

2. The catheter assembly of claim 1, wherein the one or more protrusions comprise multiple resilient catch features, wherein the catch features are spaced apart about an outer circumference of the septum housing.

3. The catheter assembly of claim 1, wherein an exterior of the catheter adapter comprises a safety mechanism engagement feature, wherein the safety mechanism engagement feature includes another groove configured to selectively couple with a V-clip, wherein the another groove is spaced apart from the groove.

4. The catheter assembly of claim 1, wherein the septum and the septum housing are disposed proximal to the side port.

5. The catheter assembly of claim 1, further comprising an introducer needle, wherein the septum housing is configured to be retained within the catheter adapter when the introducer needle is withdrawn proximally through the catheter adapter and the septum.

6. The catheter assembly of claim 1, wherein the septum comprises a distal piece and a proximal piece proximate the distal piece.

7. The catheter assembly of claim 1, wherein the distal end of the septum is not disposed within the septum housing.

8. The catheter assembly of claim 1, wherein the distal end of the septum is secured within the lumen of the catheter adapter by a friction fit.

* * * * *